US 7,373,938 B2

(12) United States Patent
Nichols et al.

(10) Patent No.: US 7,373,938 B2
(45) Date of Patent: *May 20, 2008

(54) DISPOSABLE AEROSOL GENERATOR SYSTEM AND METHODS FOR ADMINISTERING THE AEROSOL

(75) Inventors: Walter A. Nichols, Chesterfield, VA (US); F. Murphy Sprinkel, Jr., Glen Allen, VA (US)

(73) Assignee: Philip Morris USA Inc., Richmond, VA (US)

( * ) Notice: Subject to any disclaimer, the term of this patent is extended or adjusted under 35 U.S.C. 154(b) by 217 days.

This patent is subject to a terminal disclaimer.

(21) Appl. No.: 10/890,233

(22) Filed: Jul. 14, 2004

(65) Prior Publication Data

US 2004/0255941 A1  Dec. 23, 2004

Related U.S. Application Data

(63) Continuation of application No. 09/742,321, filed on Dec. 22, 2000, now Pat. No. 6,799,572.

(51) Int. Cl.
 *A61M 16/00* (2006.01)
 *F23D 11/00* (2006.01)
(52) U.S. Cl. ............................ 128/203.26; 128/203.17; 128/203.27
(58) Field of Classification Search .......... 128/203.12, 128/203.17, 203.25, 203.27, 203.28, 203.15, 128/203.21, 203.26
See application file for complete search history.

(56) References Cited

U.S. PATENT DOCUMENTS 2,896,856 A   7/1959  Kravits 3,084,698 A   4/1963  Smith (Continued)

FOREIGN PATENT DOCUMENTS

BE           354004 A    9/1928

(Continued)

OTHER PUBLICATIONS

Notification of Transmittal of the International Search Report or the Declaration dated Mar. 6, 2003 for PCT/US02/38910.

(Continued)

*Primary Examiner*—Michael J. Hayes
*Assistant Examiner*—Michael G. Mendoza
(74) *Attorney, Agent, or Firm*—Buchanan Ingersoll & Rooney PC

(57) ABSTRACT

A disposable aerosol generator for use with an inhaler device which includes a heater adapted to volatilize fluid stored in the disposable aerosol generator and method of using the inhaler. The disposable body includes a sealed chamber and an outlet, the chamber being located between first and second layers of material. The chamber holds a predetermined volume of a fluid which is expelled through the outlet when the fluid in the chamber is volatilized by the heater. The disposable body can include a series of spaced apart aerosol generators, each of which can be advanced to a release position at which the heater can heat one of the fluid containing chambers. Prior to heating the fluid, the outlet can be formed by severing the first and/or second layer with a piercing element and the volatilized fluid can be expelled from the outlet into a passage of a dispensing member.

9 Claims, 2 Drawing Sheets

U.S. PATENT DOCUMENTS

| | | |
|---|---|---|
| 3,157,179 A | 11/1964 | Paullus et al. |
| 3,162,324 A | 12/1964 | Houser |
| 3,431,393 A | 3/1969 | Katsuda |
| 3,486,663 A | 12/1969 | Humphrey |
| 3,658,059 A | 4/1972 | Steil |
| 3,716,416 A | 2/1973 | Adlhart et al. |
| 3,750,961 A | 8/1973 | Franz |
| 3,847,304 A | 11/1974 | Cohen |
| 3,859,398 A | 1/1975 | Havstad |
| 3,902,635 A | 9/1975 | Jinotti |
| 3,903,883 A | 9/1975 | Pecina et al. |
| 3,904,083 A | 9/1975 | Little |
| 3,967,001 A | 6/1976 | Almaula et al. |
| 3,987,941 A | 10/1976 | Blessing |
| 3,993,246 A | 11/1976 | Erb et al. |
| 4,012,471 A | 3/1977 | Kunkle, Jr. |
| 4,012,472 A | 3/1977 | Lindsey |
| 4,012,473 A | 3/1977 | Lindsey et al. |
| 4,042,153 A | 8/1977 | Callahan et al. |
| 4,060,082 A | 11/1977 | Lindberg et al. |
| 4,077,542 A | 3/1978 | Petterson |
| 4,161,282 A | 7/1979 | Erb et al. |
| 4,162,501 A | 7/1979 | Mitchell et al. |
| 4,215,708 A | 8/1980 | Bron |
| 4,231,492 A | 11/1980 | Rios |
| 4,258,073 A | 3/1981 | Payne |
| 4,261,356 A | 4/1981 | Turner et al. |
| 4,289,003 A | 9/1981 | Yang |
| 4,291,838 A | 9/1981 | Williams |
| 4,303,083 A | 12/1981 | Burruss, Jr. |
| 4,383,171 A | 5/1983 | Sinha et al. |
| 4,391,308 A | 7/1983 | Steiner |
| 4,395,303 A | 7/1983 | Weir |
| 4,433,797 A | 2/1984 | Galia |
| 4,471,892 A | 9/1984 | Coleman |
| 4,512,341 A | 4/1985 | Lester |
| 4,575,609 A | 3/1986 | Fassel et al. |
| 4,627,432 A | 12/1986 | Newell et al. |
| 4,649,911 A | 3/1987 | Knight et al. |
| 4,682,010 A | 7/1987 | Drapeau et al. |
| 4,695,625 A | 9/1987 | Macdonald |
| 4,700,657 A | 10/1987 | Butland |
| 4,730,111 A | 3/1988 | Vestal et al. |
| 4,735,217 A | 4/1988 | Gerth et al. |
| 4,744,932 A | 5/1988 | Browne |
| 4,749,778 A | 6/1988 | Fukuzawa et al. |
| 4,753,352 A | 6/1988 | Dauphin et al. |
| 4,753,758 A * | 6/1988 | Miller ........................ 261/139 |
| 4,762,995 A | 8/1988 | Browner et al. |
| 4,776,515 A | 10/1988 | Michalchik |
| 4,790,305 A | 12/1988 | Zoltan et al. |
| 4,811,731 A | 3/1989 | Newell et al. |
| 4,819,625 A | 4/1989 | Howe |
| 4,819,834 A | 4/1989 | Thiel |
| 4,829,996 A | 5/1989 | Noakes et al. |
| 4,837,260 A | 6/1989 | Sato et al. |
| 4,848,374 A | 7/1989 | Chard et al. |
| 4,864,044 A | 9/1989 | Lewis et al. |
| 4,871,115 A | 10/1989 | Hessey |
| 4,871,623 A | 10/1989 | Hoopman et al. |
| 4,877,989 A | 10/1989 | Drews et al. |
| 4,911,157 A | 3/1990 | Miller |
| 4,922,901 A | 5/1990 | Brooks et al. |
| 4,926,852 A | 5/1990 | Zoltan et al. |
| 4,935,624 A | 6/1990 | Henion et al. |
| 4,941,483 A | 7/1990 | Ridings et al. |
| 4,947,875 A | 8/1990 | Brooks et al. |
| 4,974,754 A | 12/1990 | Wirz |
| 4,982,097 A | 1/1991 | Slivon et al. |
| 4,992,206 A | 2/1991 | Waldron |
| 5,021,802 A | 6/1991 | Allred |
| 5,044,565 A | 9/1991 | Alexander |
| 5,056,511 A | 10/1991 | Ronge |
| 5,060,671 A | 10/1991 | Counts et al. |
| 5,063,921 A | 11/1991 | Howe |
| 5,096,092 A | 3/1992 | Devine |
| 5,125,441 A | 6/1992 | Mette |
| 5,133,343 A | 7/1992 | Johnson, IV et al. |
| 5,134,993 A | 8/1992 | van der Linden et al. |
| 5,135,009 A | 8/1992 | Müller et al. |
| 5,144,962 A | 9/1992 | Counts et al. |
| 5,151,827 A | 9/1992 | Ven et al. |
| 5,178,305 A | 1/1993 | Keller |
| 5,184,776 A | 2/1993 | Minier |
| 5,217,004 A | 6/1993 | Blasnik et al. |
| 5,226,441 A | 7/1993 | Dunmire et al. |
| 5,228,444 A | 7/1993 | Burch |
| 5,230,445 A | 7/1993 | Rusnak |
| 5,231,983 A | 8/1993 | Matson et al. |
| 5,259,370 A | 11/1993 | Howe |
| 5,290,540 A | 3/1994 | Prince et al. |
| 5,298,744 A | 3/1994 | Mimura et al. |
| 5,299,565 A | 4/1994 | Brown |
| 5,322,057 A | 6/1994 | Raabe et al. |
| 5,327,915 A | 7/1994 | Porenski et al. |
| 5,342,180 A | 8/1994 | Daoud |
| 5,342,645 A | 8/1994 | Eisele et al. |
| 5,349,946 A | 9/1994 | McComb |
| 5,395,445 A | 3/1995 | Bohanan |
| 5,409,104 A | 4/1995 | Lovell |
| 5,421,489 A | 6/1995 | Holzner, Sr. et al. |
| 5,462,597 A | 10/1995 | Jubran |
| 5,474,059 A | 12/1995 | Cooper |
| 5,515,842 A | 5/1996 | Ramseyer et al. |
| 5,522,385 A | 6/1996 | Lloyd et al. |
| 5,556,964 A | 9/1996 | Hofstraat et al. |
| 5,564,442 A | 10/1996 | MacDonald et al. |
| 5,565,677 A | 10/1996 | Wexler |
| 5,575,929 A | 11/1996 | Yu et al. |
| 5,585,045 A | 12/1996 | Heinonen et al. |
| 5,611,846 A | 3/1997 | Overton et al. |
| 5,617,844 A | 4/1997 | King |
| 5,622,166 A | 4/1997 | Eisele et al. |
| 5,642,728 A | 7/1997 | Andersson et al. |
| 5,674,860 A | 10/1997 | Carling et al. |
| 5,682,874 A | 11/1997 | Grabenkort et al. |
| 5,730,158 A | 3/1998 | Collins et al. |
| 5,743,250 A | 4/1998 | Gonda et al. |
| 5,743,251 A | 4/1998 | Howell et al. |
| 5,756,995 A | 5/1998 | Maswadeh et al. |
| 5,765,724 A | 6/1998 | Amberg et al. |
| 5,792,422 A | 8/1998 | Lin et al. |
| 5,823,178 A | 10/1998 | Lloyd et al. |
| 5,839,430 A | 11/1998 | Cama |
| 5,855,202 A | 1/1999 | Andrade |
| 5,856,671 A | 1/1999 | Henion et al. |
| 5,863,652 A | 1/1999 | Matsumura et al. |
| 5,869,133 A | 2/1999 | Anthony et al. |
| 5,872,010 A | 2/1999 | Karger et al. |
| 5,875,776 A | 3/1999 | Vaghefi |
| 5,878,752 A | 3/1999 | Adams et al. |
| 5,881,714 A | 3/1999 | Yokoi et al. |
| 5,906,202 A | 5/1999 | Schuster et al. |
| 5,914,122 A | 6/1999 | Otterbeck et al. |
| 5,932,249 A | 8/1999 | Gruber et al. |
| 5,932,315 A | 8/1999 | Lum et al. |
| 5,934,272 A | 8/1999 | Lloyd et al. |
| 5,934,273 A | 8/1999 | Andersson et al. |
| 5,944,025 A | 8/1999 | Cook et al. |
| 5,954,979 A | 9/1999 | Counts et al. |
| 5,957,124 A * | 9/1999 | Lloyd et al. ........... 128/200.22 |
| 5,970,973 A | 10/1999 | Gonda et al. |
| 5,970,974 A | 10/1999 | Van Der Linden et al. |
| 5,978,548 A | 11/1999 | Holmstrand et al. |

| | | |
|---|---|---|
| 5,993,633 A | 11/1999 | Smith et al. |
| 6,014,970 A | 1/2000 | Ivri et al. |
| 6,053,176 A | 4/2000 | Adams et al. |
| 6,054,032 A | 4/2000 | Haddad et al. |
| 6,069,214 A | 5/2000 | McCormick et al. |
| 6,069,219 A | 5/2000 | McCormick et al. |
| 6,070,575 A | 6/2000 | Gonda et al. |
| 6,071,428 A | 6/2000 | Franks et al. |
| 6,076,522 A | 6/2000 | Dwivedi et al. |
| 6,077,543 A | 6/2000 | Gordon et al. |
| 6,080,721 A | 6/2000 | Patton |
| 6,085,740 A | 7/2000 | Ivri et al. |
| 6,085,753 A | 7/2000 | Gonda et al. |
| 6,089,228 A | 7/2000 | Smith et al. |
| 6,095,153 A | 8/2000 | Kessler et al. |
| 6,098,615 A | 8/2000 | Lloyd et al. |
| 6,098,620 A | 8/2000 | Lloyd et al. |
| 6,103,270 A | 8/2000 | Johnson et al. |
| 6,116,238 A | 9/2000 | Jackson et al. |
| 6,116,516 A | 9/2000 | Gañán-Calvo |
| 6,116,893 A | 9/2000 | Peach |
| 6,119,953 A | 9/2000 | Gañán-Calvo et al. |
| 6,123,068 A | 9/2000 | Lloyd et al. |
| 6,123,936 A | 9/2000 | Platz et al. |
| 6,131,567 A | 10/2000 | Gonda et al. |
| 6,131,570 A | 10/2000 | Schuster et al. |
| 6,136,346 A | 10/2000 | Eljamal et al. |
| 6,138,668 A | 10/2000 | Patton et al. |
| 6,155,268 A | 12/2000 | Takeuchi |
| 6,158,431 A | 12/2000 | Poole |
| 6,158,676 A | 12/2000 | Hughes |
| 6,159,188 A | 12/2000 | Laibovitz et al. |
| 6,164,630 A | 12/2000 | Birdsell et al. |
| 6,165,463 A | 12/2000 | Platz et al. |
| 6,167,880 B1 | 1/2001 | Gonda et al. |
| 6,174,469 B1 | 1/2001 | Gañán-Calvo |
| 6,182,712 B1 | 2/2001 | Stout et al. |
| 6,187,214 B1 | 2/2001 | Gañán-Calvo |
| 6,187,344 B1 | 2/2001 | Eljamal et al. |
| 6,189,803 B1 | 2/2001 | Gañán-Calvo |
| 6,192,882 B1 | 2/2001 | Gonda |
| 6,196,219 B1 * | 3/2001 | Hess et al. ............. 128/200.21 |
| 6,197,835 B1 | 3/2001 | Gañán-Calvo |
| 6,205,999 B1 | 3/2001 | Ivri et al. |
| 6,206,242 B1 | 3/2001 | Amberg et al. |
| 6,207,135 B1 | 3/2001 | Rössling et al. |
| 6,223,746 B1 | 5/2001 | Jewett et al. |
| 6,230,706 B1 | 5/2001 | Gonda et al. |
| 6,231,851 B1 | 5/2001 | Platz et al. |
| 6,234,167 B1 | 5/2001 | Cox et al. |
| 6,234,402 B1 | 5/2001 | Gañán-Calvo |
| 6,235,177 B1 | 5/2001 | Borland et al. |
| 6,250,298 B1 | 6/2001 | Gonda et al. |
| 6,250,301 B1 | 6/2001 | Pate |
| 6,257,233 B1 | 7/2001 | Burr et al. |
| 6,258,341 B1 | 7/2001 | Foster et al. |
| 6,263,872 B1 | 7/2001 | Schuster et al. |
| 6,267,155 B1 | 7/2001 | Parks et al. |
| 6,275,650 B1 | 8/2001 | Lambert |
| 6,276,347 B1 | 8/2001 | Hunt |
| 6,284,525 B1 | 9/2001 | Mathies et al. |
| 6,288,360 B1 | 9/2001 | Beste |
| 6,290,685 B1 | 9/2001 | Insley et al. |
| 6,294,204 B1 | 9/2001 | Rössling et al. |
| 6,295,986 B1 | 10/2001 | Patel et al. |
| 6,318,361 B1 | 11/2001 | Sosiak |
| 6,367,473 B1 | 4/2002 | Kafer |
| 6,378,518 B1 | 4/2002 | Miekka et al. |
| 6,681,769 B2 * | 1/2004 | Sprinkel et al. ....... 128/203.26 |
| 6,701,921 B2 * | 3/2004 | Sprinkel et al. ....... 128/203.26 |

FOREIGN PATENT DOCUMENTS

| | | |
|---|---|---|
| BE | 354094 A | 9/1928 |
| DE | 1036470 B1 | 8/1958 |
| EP | 0358114 A | 3/1990 |
| EP | 0642802 A2 | 5/1996 |
| FR | 667979 A | 10/1929 |
| HU | 168128 B | 11/1977 |
| HU | 216121 B | 3/1991 |
| HU | 207457 A | 4/1993 |
| HU | P953409 | 6/1994 |
| WO | 94/09842 A | 5/1994 |
| WO | 98/17131 | 4/1998 |

OTHER PUBLICATIONS

Notification of Transmittal of the International Search Report or the Declaration for PCT/US01/44809 dated May 8, 2003.

Written Opinion dated Nov. 4, 2003 for PCT/US01/44809.

Written Opinion dated Dec. 24, 2003 for PCT/US02/38910.

Barry, P.W. et al. "In Vitro Comparison of the Amount of Salbutamol Available for Inhalation From Different Formulations Used with Different Spacer Devices" Eur Respir J 1997; 10: 1345-1348.

Byron, Peter R. Ph.D., Chairman, "Recommendations of the USP Advisory Panel on Aerosols on the USP General Chapters on Aerosols (601) and Uniformity of Dosage Units (905)", Pharmacopeial Forum, vol. 20, No. 3, pp. 7477-7505, May-Jun. 1994 (023).

Hindle, Michael et al., "High Efficiency Aerosol Production Using the Capillary Aerosol Generator" PharmSci 1998; 1: (1: suppl) S211.

Hindle, Michael et al., "High Efficiency Fine Particle Generation Using Novel Condensation Technology", Respiratory Drug Delivery VI (eds Dalby, R.N., Byron, P.R. & Farr, S.J.) Interpharm Press, Buffalo Grove, IL 1998 pp. 97-102.

Hou, Shuguang et al. *Solution Stability of Budensonide in Novel Aerosol Formulations* Abstract No. 2582, Solid State Physical Pharmacy, Nov. 17, 1998, p. S-307.

Kousaka, Yasuo et al., "Generation of Aerosol Particles by Boiling of Suspensions", Aerosol Science and Technology, 21:236-240 (1994) (023).

Morén, Folke "Drug Deposition of Pressurized Inhalation Aerosols I. Influence of Actuator Tube Design" AB Draco (Subsidiary of AB Astra, Sweden) Research and Development Laboratories Pack, S-221 01 Lund (Sweden), International Journal of Pharmaceutrics, 1 (1978) 205-212.

Newman, Stephen P. et al. "Deposition of Pressurized Suspension Aerosols Inhaled Through Extension Devices[1-3]" Am Rev Respir Dis 1981; 124:317-320.

Roth, G. et al. High Performance Liquid Chromatographic Determination of Epimers, Impurities, and Content of the Glucocorticoid Budesonide and Preparation of Primary Standard, Journal of Pharmaceutical Sciences, vol. 69, No. 7, pp. 766-770, Jul. 1980.

International Preliminary Examination Report dated Feb. 8, 2005 for PCT/US01/44809.

Notification of Transmittal of International Preliminary Examination Report dated Dec. 8, 2004 for PCT/US02/38910.

* cited by examiner

DISPOSABLE AEROSOL GENERATOR SYSTEM AND METHODS FOR ADMINISTERING THE AEROSOL

This application is a continuation application of U.S. application Ser. No. 09/742,321 entitled DISPOSABLE AEROSOL GENERATOR SYSTEM AND METHODS FOR ADMINISTERING THE AEROSOL, filed on Dec. 22, 2000, now U.S. Pat. No. 6,799,572 the entire contents of which is hereby incorporated by reference.

BACKGROUND OF THE INVENTION

1. Field of the Invention

The present invention relates to an apparatus, system and methods of administering a fluid such as a medicated fluid in metered amount such as a unit dose to treat respiratory ailments. In particular, the invention relates to disposable aerosol generators, wherein the aerosols are generated via vaporization.

2. Description of Related Art

Aerosols are useful in a variety of applications including treatment of respiratory ailments. Various techniques for generating aerosols are disclosed in U.S. Pat. Nos. 4,811,731; 4,627,432; 5,743,251; and 5,823,178.

In particular, two distinct methods for delivery of medicated fluid in the form of an aerosol have been developed. In accordance with one method, a pharmaceutically active drug is dispensed in a low boiling point propellant (e.g., chloro-fluoro-carbon (CFC) or (HFA)) loaded in a pressurized canister from which the drug/propellant formulation may be released by the use of a device generally known as a metered dose inhaler. Once released the propellant evaporates and particles of the drug are inhaled by the patient. The other method involves the use of a nebulizer which creates an inhalable mist of fine particles from a solution or suspension of a drug. Both methods are hindered by significant problems relating to administering the proper dose.

In drug delivery applications, it is typically desirable to provide an aerosol having average mass median particles diameter of less than 2 microns to facilitate deep lung penetration. Additionally, it is desirable, in certain drug applications, to deliver medicaments at high flow rates (i.e., above 1 milligram per second). Devices for controlling the flow rate of an aerosol are known. For example, U.S. Pat. No. 4,790,305 concerns controlling the particle size of a metered dose of aerosol for delivery to the walls of bronchi and bronchioles by filling a first chamber with medication and a second chamber with air such that all of the air is inhaled prior to the inhaling medication, and using flow control orifices to control the flow rate. U.S. Pat. No. 4,926,852 relates to metering a dose of medication into a flow-through chamber that has orifices to limit the flow rate to control particle size. U.S. Pat. No. 3,658,059 discloses a baffle that changes the size of an aperture in the passage of the suspension being inhaled to select the quantity and size of particles delivered. A problem associated with these devices is that they process the aerosol after it is generated and are inefficient and wasteful.

To meet the requirements of administering a fluid in the form of an aerosol and to overcome the disadvantages of the prior art, it is an object of the present invention to provide an aerosol generator which vaporizes the fluid at a controlled flow rate regardless of the fluid's viscosity.

It is another object of the invention to obtain uniform vaporization of the fluid that is expelled from the aerosol generator.

It is a further object of the invention to provide a disposable aerosol generator which can deliver a metered dose of the fluid. By delivering individual single doses of medicated fluid it is possible to avoid contamination of the fluid, thereby negating the need for bacteriostatic compounds within the drug formulation.

It is yet another object of the invention to provide a disposable cartridge which can incorporate a package having therein multiple disposable aerosol generators, each of which provides a single shot delivery, as required by the user.

Other objects and aspects of the present invention will become apparent to one of ordinary skill in the art upon review of the specification, drawings and claims appended hereto.

SUMMARY OF THE INVENTION

According to one aspect of the invention, a disposable aerosol generator is provided which is adapted for use with an inhaler device which includes a heater arranged to volatilize fluid stored in the disposable aerosol generator. The aerosol generator comprises a disposable body having a sealed chamber and an outlet wherein first and second layers of material define the chamber. The chamber accommodates a predetermined volume of a fluid which is expelled through the outlet when the fluid in the chamber is volatilized by the heater.

According to another aspect of the invention, an inhaler device is provided which is usable with the disposable aerosol generator mentioned above, the inhaler device including a heater arranged to heat the fluid in the chamber so as to expel volatilized fluid from the outlet. The heater can comprise a layer of resistance heating material on a substrate which includes an opening located adjacent the outlet. In order to form the outlet, an opening device such as a piercing element can be provided which is adapted to pierce the first and/or second layer to form the outlet.

According to a further aspect of the invention, a method of using the inhaler device mentioned above is provided, the method including severing the first and/or second layer so as to form the outlet and activating the heater so as to volatilize the fluid in the chamber and expel the volatilized fluid through the outlet. According to a preferred method, the disposable body includes a series of spaced apart aerosol generators and the method includes moving the disposable body relative to the inhaler device so as to locate a first one of the aerosol generators at a position where the heater can heat the fluid in the chamber of the first aerosol generator and volatilize the fluid therein. The severing can be carried out by driving a piercing member through the first and/or second layer and the outlet can be located adjacent a passage of a dispensing member such that the volatilized fluid formed by the heater is expelled into the passage after passing through the outlet.

BRIEF DESCRIPTION OF THE DRAWINGS

The objects and advantages of the invention will become apparent from the following detailed description of the preferred embodiments thereof in connection with the accompanying drawing, in which.

DETAILED DESCRIPTION OF THE PREFERRED EMBODIMENTS OF THE INVENTION

The present invention provides an inhaler effective for administering a fluid such as a medicated fluid in aerosol form. It has surprisingly and unexpectedly been determined that a metered amount of fluid can be delivered from the inhaler via a disposable aerosol generator wherein the fluid is fully vaporized and delivered at a predetermined flow rate.

Figure 1:
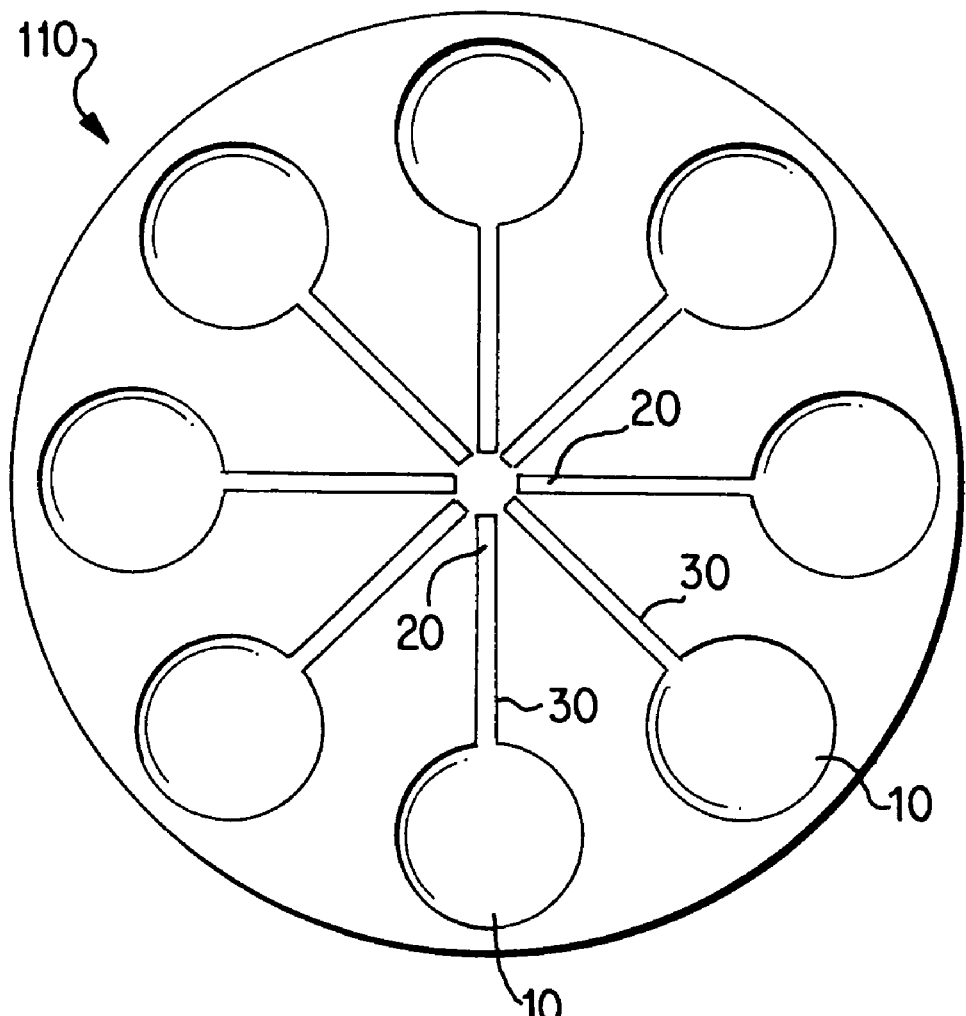
FIGS. 1 and 2 show details of a disposable body containing a series of aerosol generators according to one embodiment of the invention, FIG. 1 showing a top view thereof and FIG. 2 showing a side view thereof.
Figure 2:
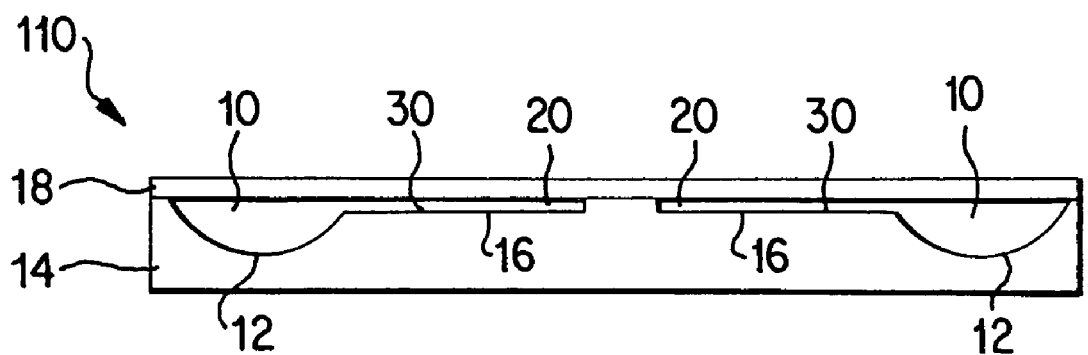
Figure 3:
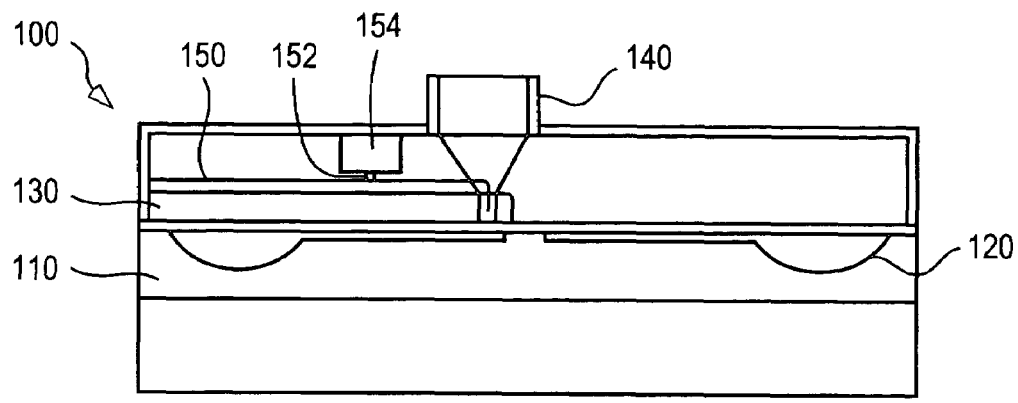
FIG. 3 shows an inhaler device according to an embodiment of the invention.
Figure 4:
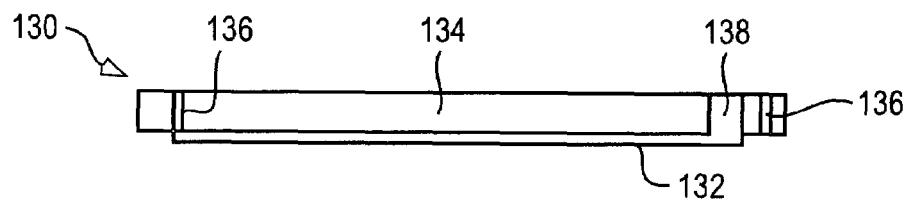
FIG. 4 shows details of a heater of the inhaler device shown in FIG. 3.

With reference to FIGS. 1 and 2, an aerosol generator in accordance with one embodiment of the present invention is shown schematically. A single shot chamber or reservoir 10 is designed to accommodate a predetermined volume of fluid which can incorporate a medicant for treating various respiratory ailments (e.g., a partial list includes albuterol, isoproterenol sulfate, metaproterenol sulfate, terbutaline sulfate, pirbuterol acetate, salmeterol xinotoate, formotorol; steroids including beclomethasone dipropionate, flunisolide, fluticasone, budesonide and triamcinolone acetonide, beclomethasone dipropionate, triamcinolone acetonide, flunisolide and fluticasone, etc.). Of course, the volume and composition of fluid may be predicated on the amount desired to treat a particular medical ailment.

An outlet 20 is in fluid communication with the chamber 10 and a heating member (not shown) disposed on or in proximate location to either chamber 10 and/or outlet 20 is operable to vaporize the fluid in the chamber 10 and eject the vaporized fluid out of the outlet 20. For instance, a heating member may be employed in conjunction with both the chamber 110 and outlet 120. In a preferred embodiment, the heater comprises part of a reusable inhaler device. However, the heater can be incorporated in the disposable body, e.g., a resistance heating element heated by passing current therethrough or by inductively heating the heating element.

In accordance with a preferred embodiment of the invention, chamber 10 is constructed from a material (e.g., polymeric, aluminum foil) resistant to heating. For example, in the embodiment shown in FIGS. 1 and 2, the chamber 10 is formed as a recess 12 in an injection molded body 14 of polymer material and a flow passage 30 comprises a channel 16 in the body 14, the channel 16 extending from the recess 12. The chamber 10 is sealed by a layer 18 such as aluminum foil heat sealed to the plastic body 14.

In order to provide multiple doses of medicated fluid in a disposable part of an inhaler, the plastic body 14 can include a plurality of recesses 12. The laminate thus described is capable of withstanding the pressure applied to the interior of the chamber through the application of heat necessary to vaporize the fluid contained therein. Outlet 20 is preferably a small aperture at the end of the flow passage 30, the outlet being initially closed to the atmosphere. The flow passage 30 can have any suitable size which is effective to expel the vaporized fluid into the atmosphere and form the aerosol of desired particle size. For instance, flow passage 30 can have an inside diameter of about 0.05 to about 0.60 millimeter, preferably about 0.2 mm and a length of about 100 to 200 times the inside diameter. The chamber 10 can have any desired size such as a size suitable to deliver a single dose of medicated fluid, e.g., 5 μl.

In operation, the fluid in the chamber 10 is heated by a heating device which heats the fluid to a temperature sufficient to volatilize the fluid. In the case of an organic liquid material, the heating device preferably heats the fluid to approximately the boiling point, and preferably does not heat the fluid above 400° C., as most organic fluids are not stable when they are exposed to temperatures above 400° C.

Heating can be achieved in various ways including resistance or induction heating to heat the fluid via thermal conduction. Suitable heating devices envisioned for employment in the aerosol generator of the present invention include electrical resistance heaters, deposited resistance heating material such as thin platinum layers, electro-induction heating coils, etc. For example, the heating device can comprise an electrical resistance heater element arranged to thermally conduct heat into the chamber 10. The heater can be any suitable material such as platinum, tungsten, molybdenum or metal alloy such as an iron-based alloy having 71.7% (by weight) iron, 23% chromium, and 5.3% aluminum.

The flow passage 30 can have any desired configuration. For instance, the flow passage can have a uniform cross-sectional area along the length thereof between the chamber 10 and the outlet 20. However, the flow passage can vary in size along the length thereof, e.g., tapered so as to become more narrow in a direction towards the outlet 20. Further, the chamber need not comprise a concave circular recess but rather, can comprise any desired configuration sized to accommodate a single dose of the medicated fluid.

According to a preferred embodiment, the heater device can comprise a layer of resistance heating material deposited on the outside of a support member such as a plastic or ceramic member, e.g., alumina, glass, titania, zirconia, or yttria-stabilized zirconia which does not experience oxidation at normal operating temperatures.

The heater support and the heater layer preferably have a roughly matching coefficient of thermal expansion to minimize thermally induced delamination. Also, the ceramic support material can have a surface roughness to improve adhesion of the deposited heater layer. Platinum is desirable as a heater material in that it is resistant to oxidation degradation or other corrosion.

The heater layer can be deposited as a thin film on a ceramic support such that the heater layer has a thickness of, e.g., less than approximately 2 μm. The heater layer can be deposited onto the ceramic by any suitable method such as DC magnetron sputter deposition, e.g., using an HRC magnetron sputter deposition unit, in argon at $8.0 \times 10^{-3}$ Torr. Alternatively, other conventional techniques such as vacuum evaporation, chemical deposition, electroless plating, electroplating, and chemical vapor deposition can be employed to apply the heater layer to the substrate. It will be appreciated by those skilled in the art, that the energy produced by the heating device can be distributed optimally by tailoring the pattern of the thin film. For example, the heater pattern can be arranged to provide more heat near the outlet 20 than in the vicinity of the recess 12.

The closed end of the flow passage 20 can be opened by an opening device such as solenoid activated puncturing element. Alternatively, a cutting blade or scissors suitable for cutting the material sealing the flow passage 30 can be used to expel the volatilized fluid. It is further within the scope of the invention that other techniques such as a breakable seal can be employed on the closed end of the flow passage. The volatilized fluid can be expelled in a controlled manner taking into account properties of the fluid and the amount of heat needed to vaporize the fluid. The volatilized fluid can be expelled from the outlet 20 at a high velocity, e.g., approximately 90 m/s, but the volatilized fluid can be quickly dissipated in the atmosphere as the aerosol is formed from the condensing vapor, e.g., within about 2 mm of the outlet 20. The volatilized fluid can be mixed with ambient air in an inhaler mouthpiece surrounding the outlet 20, whereupon rapid cooling and condensation of the vapor result in formation of the aerosol.

The characteristics of the aerosol generated in accordance with the invention is a function of various parameters of the generator and the fluid provided. For aerosols intended for inhalation, for example, it is desirable for the aerosol to be approximately at body temperature when inhaled and for the mass media particles of the aerosol to be less than 2 microns, preferably between 0.5 and 1 micron.

Upon delivery of the metered amount of fluid, in aerosol form, the aerosol generator comprising the chamber 10, outlet 20 and flow passage 30 can be discarded. In the case where multiple generators are provided in a multidose cartridge such as the disposable body shown in FIGS. 1 and 2, the cartridge can be disposed of when the last of the individual chambers have been emptied.

In accordance with another preferred embodiment, the heating device can comprise a plurality of heating members arranged to heat the fluid in the chamber and/or along the flow passage. Also, the fluid in the chamber could be expelled mechanically, e.g., by a member which pushes the fluid into the flow passage and a heater along the flow passage can be used to volatilize the fluid and expel the vaporized fluid out of the outlet 20.

With reference to FIGS. 3-6, a fluid delivery system is depicted, wherein individual disposable aerosol generators are transported to a fluid release position as required by the user. System 100 includes a cartridge 110 loaded with disposable aerosol generators 120. In a preferred embodiment, the aerosol generators 120 are provided in the form of packets, preferably constructed as described above in connection with FIGS. 1 and 2. A heating device 130 provides sufficient energy to each generator 120 to vaporize the fluid and expel the vaporized fluid through a passage in a dispenser 140. An opening device 150 can comprise a puncture element 152 activated by a solenoid 154, the puncture element 152 being operable by a suitable controller and circuitry to penetrate the layer 18 in the vicinity of outlet 20.

The heating device 130 includes an electrically resistive heating element 132 on a substrate 134, the heating element 132 being powered by electrically conductive connections 136 extending through vias in the substrate 134. The substrate 134 includes an opening 138 through which the piercing end of the puncture element 152 can move towards and away from the cartridge 110. In operation, the controller can be activated to operate the system 100 so as to rotate is the cartridge 110 to a drug release position, actuate the solenoid to drive the puncture arm towards the cartridge so as to pierce the channel 16 and thereby form the outlet 20, and activate the heating element so as to heat the fluid in the chamber 10 whereby vaporized fluid is expelled through the dispenser 140.

Figure 5:
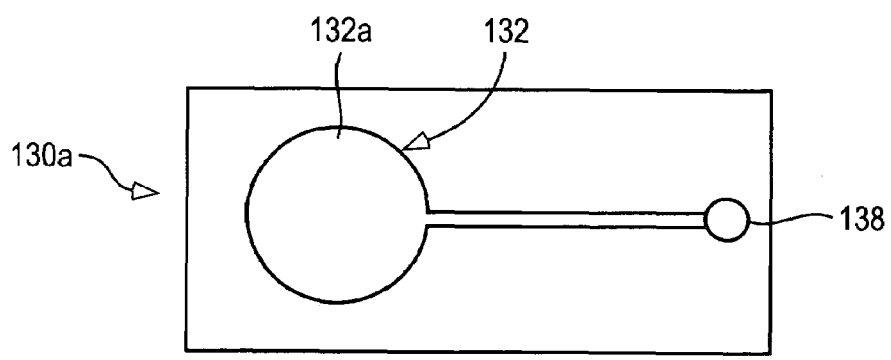
FIG. 5 shows details of a first heater pattern which can be used for a resistance heating layer in the heater shown in FIG. 4.
Figure 6:
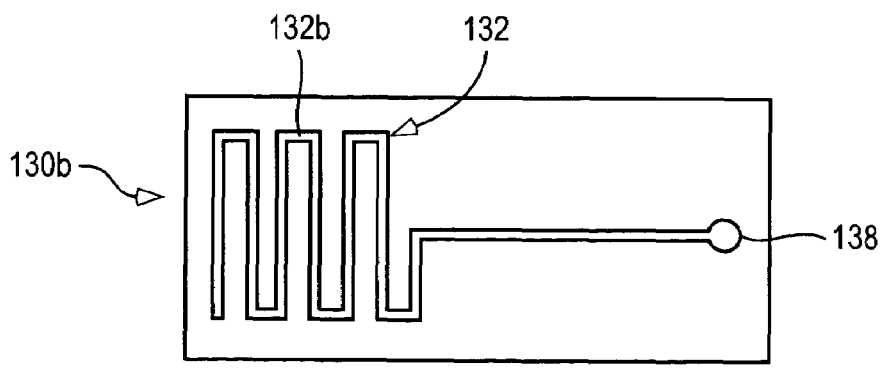
FIG. 6 shows details of a second heater pattern which can be used for a resistance heating layer in the heater shown in FIG. 4.

FIGS. 5 and 6 show embodiments of different heater patterns for the heater 130. The heater 130a shown in FIG. 5 includes a heating element 132a configured to completely cover the chamber 10 and flow passage 30. With the heater element pattern shown in FIG. 5, greater heating can be achieved in the flow passage 30 due to the smaller cross sectional area of the heating element along the flow passage. The heater 132b shown in FIG. 6 includes a heating element 132b configured as a sinusoidally shaped strip which overlies chamber 10 and a rectilinear strip which overlies the flow passage 20.

In operation, the disposable cartridge 110 can be loaded into the inhaler 100, and a transport mechanism (not shown) can be operated to successively transport the aerosol generators to the release position at which the heater volatilizes the fluid contained in the respective chamber. Driving power for the transport mechanism, the solenoid and the heating element can be provided by a power source such as a 9-volt battery. The dispenser 140 can be arranged to supply the vaporized fluid to a mouthpiece (not shown) of the inhaler 100.

While the invention has been described in detail with reference to specific embodiments thereof, it will be apparent to those skilled in the art that various changes and modifications can be made, and equivalents employed, without departing from the scope of the appended claims.

The invention claimed is:

1. An inhaler comprising:
   a heater; and
   a flow passage located in a disposable body, the disposable body comprising first and second layers of material defining the flow passage and an outlet through which volatilized fluid is expelled when the fluid is volatilized by the heater, the disposable body comprising a disc including a series of spaced apart aerosol generators, each respective aerosol generator including a sealed chamber containing fluid to be volatilized, each sealed chamber being in fluid communication with the flow passage and located adjacent an outer portion of the disc with the outlet of each respective aerosol generator being located adjacent a central portion of the disc;
   wherein the heater is operable to volatilize fluid and produce aerosol at a predetermined flow rate.

2. The inhaler according to claim 1, wherein the heater comprises a layer of resistance heating material on a substrate, the substrate including an opening located adjacent the outlet of each respective aerosol generator or a respective one of the aerosol generators.

3. The inhaler according to claim 2, further comprising an opening device, the opening device being adapted to pierce the first layer and/or second layer and open the outlet of each respective aerosol generator or a respective one of the aerosol generators.

4. The inhaler according to claim 3, wherein the opening device includes a solenoid activated piercing element, the piercing element including a movable tip which is located in the opening in the substrate, the tip being moved upon actuation of the piercing element such that the tip penetrates the first layer of the disposable body.

5. The inhaler according to claim 1, wherein the disposable body is movably supported such that the chamber of each respective aerosol generator or a respective one of the aerosol generators can be moved to a release position at which the heater can heat the fluid in the respective chamber sufficiently to volatilize the fluid to expel the volatilized fluid through the opened outlet.

6. The inhaler according to claim 2, wherein the layer of resistance heating material comprises a strip arranged in a pattern which is coextensive with the size of the chamber.

7. The inhaler according to claim 1, further comprising a dispensing member located adjacent the outlet of each respective aerosol generator or a respective one of the aerosol generators, the volatilized fluid expelled from the opened outlet passing through a passage in the dispensing member.

8. The inhaler according to claim 1, wherein the disposable body being configured to fit in the inhaler so as to allow advancement of each respective aerosol generator to a release position at which the heater can heat the fluid in the chamber of the respective aerosol generator.

9. The inhaler according to claim 1, wherein the first layer comprises a layer of polymer material and the second layer of material comprises a foil heat sealed to the polymer layer, the inhaler including an opening member which is operable to pierce the foil layer to open the outlet of each respective aerosol generator or a respective one of the aerosol generators immediately prior to when the heater is activated to volatilize the fluid in the chamber of the respective aerosol generator.

* * * * *